United States Patent
Anderson, Jr.

(10) Patent No.: US 11,278,301 B2
(45) Date of Patent: Mar. 22, 2022

(54) RHINOTILLEXIS APPARATUS

(71) Applicant: Ronnie Anderson, Jr., Prairieville, LA (US)

(72) Inventor: Ronnie Anderson, Jr., Prairieville, LA (US)

(*) Notice: Subject to any disclaimer, the term of this patent is extended or adjusted under 35 U.S.C. 154(b) by 264 days.

(21) Appl. No.: 15/597,735

(22) Filed: May 17, 2017

(65) Prior Publication Data

US 2018/0333163 A1    Nov. 22, 2018

(51) Int. Cl.
*A61B 17/24* (2006.01)
*A61F 13/38* (2006.01)

(52) U.S. Cl.
CPC .............. *A61B 17/24* (2013.01); *A61F 13/38* (2013.01); *A61B 2017/246* (2013.01)

(58) Field of Classification Search
CPC ... A61B 17/24; A61B 2017/246; A61F 13/38; A61F 13/126; A61F 11/006
See application file for complete search history.

(56) References Cited

U.S. PATENT DOCUMENTS 6,358,231 B1 * 3/2002 Schindler ................ A61F 11/00
604/1

* cited by examiner

*Primary Examiner* — Ariana Zimbouski
(74) *Attorney, Agent, or Firm* — Williams Intellectual Property; Benjamin F. Williams

(57) ABSTRACT

A rhinotillexis apparatus, devised for controlled insertion into a nasal cavity for collection and removal of mucus therefrom, includes a spatulate head member having a first surface and a second surface convergent at an anterior edge, a neck portion, a shield member, and a handle member for dexterous wielding in the hands of a user. The head member is tautly overlain with an absorbent layer. The shield member prevents over-insertion of the head member into the nasal cavity and shields a user's hands from contamination with mucus during use. Disposal of the apparatus after single-use decreases potential for cross-contamination.

16 Claims, 5 Drawing Sheets

RHINOTILLEXIS APPARATUS

BACKGROUND OF THE INVENTION

Removal of mucus from the nasal cavity often leads to cross-contamination as mucus, and potentially pathogens therein contained, contacts the hands—either via direct contact or through tissues and other fabrics frequently employed to blow the nose. Once transferred to the hands of a user, contagions are readily spread by user contact with objects throughout the proximal environment. Cross-contamination can result when additional users interact with the proximal environment, whereby contagions are readily spread between people.

Moreover, fingers are not ideally shaped to assist in removing dried mucus from the nasal cavity and such attempts at rhinotillexis as employ the fingers may result in discomfort and, in extreme cases, even injury effected by the margo liber of the corpus unguis.

Use of other implements and foreign bodies for insertion into the nasal cavity is ill-advised.

What is needed, therefore, is a rhinotillexus apparatus specifically devised for insertion into the nasal cavity for controlled collection and removal of mucus therefrom without danger of causing damage or injury to the respiratory epithelium, nasal cochlea, vestibule, or other anatomy beyond the naris, by overextension therein.

FIELD OF THE INVENTION

The present invention relates to a rhinotillexis apparatus devised specifically or insertion into the naris and vestibule of a user's nasal cavity to collect and remove mucus from said user's nose. The present rhinotillexis apparatus includes a spatulate head member devised with an anterior edge to enable leading contact against the respiratory epithelium to absorb mucus into an absorbent layer disposed upon the spatulate head member and enable comfortable removal of mucus from the nose without causing injury thereto.

Further, the present rhinotillexis apparatus is wieldable to prevent direct contact of mucus with a user's hands. Disposal of the present rhinotillexis apparatus subsequent use further limits potential for cross-contamination. Single-use of the present rhinotillexis apparatus maintains sterility of the head member wherein pathogens are not introducible into the nasal cavity as a result of contact with the head member whereby opportunistic infections as may otherwise occur are prevented.

SUMMARY OF THE INVENTION

The present rhinotillexis apparatus has been devised to enable removal of mucus from a nasal cavity without a user having to directly contact mucus or the interior of the nasal cavity with said user's hands, whereby cross-contamination between the user and other objects and people in the proximal environment is preventable. Further, the present rhinotillexis apparatus presents an anterior edge adapted for controlled manipulation interior to the nasal cavity whereby collection and removal of mucus is facilitated without contacting said user's hands.

The present rhinotillexis apparatus, therefore, includes a spatulate head member devised for insertion into the naris of a user. The spatulate head member includes an anterior end and a posterior end. A polygonal base is disposed at the posterior end and an anterior edge is disposed at the anterior end. A first surface is disposed sloped from the posterior end to the anterior end, said first surface sloped from a maximum thickness of the head member at the base to a minimum thickness of the head member at the anterior edge.

A second surface is disposed opposite the first surface between the base and the anterior edge, said second surface convergent with the first surface at the anterior edge. A pair of generally triangular side surfaces, having adjacent and hypotenuse sides, therefore laterally delimit the head member on either side. The spatulate head member further includes a parabolic coronal cross-section with a focus disposed medially at the anterior edge. In an example embodiment set forth herein, the first surface is concave and the second surface is convex. The anterior edge is thereby wieldable by a user as a leading point of contact into the nasal cavity.

An absorbent layer is disposed overlying the head member, at least covering the first surface, second surface, and anterior edge. The absorbent layer is devised to exhibit a wicking potential (that is, wick moisture thereinto) and alternately an osmotic potential (that is draw moisture into the absorbent layer by osmotic pressure) whereby mucus exuded by the mucus membranes and respiratory epithelium is absorbed into the absorbent layer for removal, as desired. In at least one embodiment contemplated herein, the absorbent covering is flocculent and removable. In at least one embodiment of the present invention, the absorbent layer is comprised of a perforated material wherein mucus is collectable into a plurality of voids. In at least one embodiment of the present invention, the absorbent layer is coextensive with the head member.

A narrow neck portion is disposed perpendicularly rearward upon the base. The neck portion may include a diameter substantially lesser than the length of the base and thereby enable flexibility and some limited movement of head member. A shield member is transversely disposed upon the neck portion. The shield member includes a forward surface, disposed facing the head member, and a rearward surface, disposed facing away from the head member. An outer rim is disposed perimetrically bounding the shield member at an extremity radially projected beyond any bounds of the head member. The shield member thus prevents over-insertion of the head member into a naris of a user and, also, prevents mucus from contacting the hands of a user when said user wields the device.

The handle member is disposed longitudinally rearward from the rearward surface of the shield member. The handle member includes a rounded end and is configured ergonomically for manipulation by a user. The handle member is devised to conceal a user's hands behind the shield member to prevent contact with mucus while operating the device.

Thus has been broadly outlined the more important features of the present rhinotillexis apparatus so that the detailed description thereof that follows may be better understood and in order that the present contribution to the art may be better appreciated.

Objects of the present rhinotillexis apparatus, along with various novel features that characterize the invention are particularly pointed out in the claims forming a part of this disclosure. For better understanding of the rhinotillexis apparatus, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
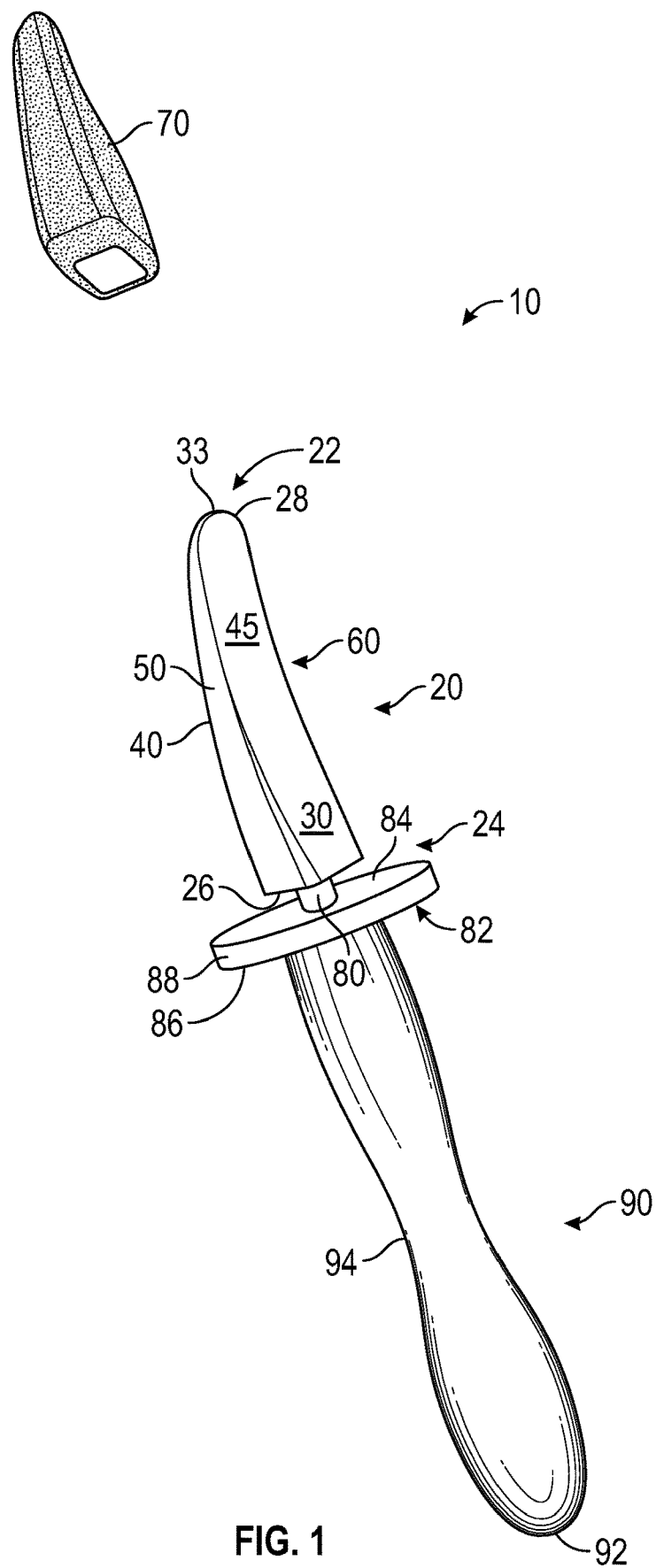
FIG. 1 is an isometric view of an example embodiment.

With reference now to the drawings, and in particular FIGS. 1 through 5 thereof, example of the instant rhinotillexis apparatus employing the principles and concepts of the present rhinotillexis apparatus and generally designated by the reference number 10 will be described.

Referring to FIGS. 1 through 5 an example embodiment of the present rhinotillexis apparatus 10 is illustrated.

The present rhinotillexis apparatus 10 has been devised to enable controlled removal of mucus from a user's nose without a user having to directly contact the ciliated pseudostratified columnar epithelium (the "respiratory epithelium"), or the pyramidal cells, goblet cells, or mucus membranes wherefrom mucus during inflammation and infection frequently exudes. The present rhinotillexis apparatus 10, therefore, enables extension of a spatulate head member 20 into the anterior naris 500 to collect mucus within the vestibule 502 for removal from the nasal cavity 506 thereby. The spatulate head member 20 includes an absorbent layer 70 disposed thereupon which sorbs mucus thereto. The rhinotillexis apparatus 10 is disposable after single-use whereby cross-contamination is preventable.

The present rhinotillexis apparatus 10, therefore, includes a spatulate head member 20 disposed anteriorly relative a handle member 90. The spatulate head member 20 includes a maximum thickness 100, at a posterior end 24, and a minimum thickness 200, at an anterior end 22. A polygonal base 26 is disposed upon the spatulate head member 20 at the posterior end 24 and an anterior edge 28 is disposed at the anterior end 22. A first surface 30 is disposed sloped from the posterior end 24 to the anterior end 22. A second surface 40 is disposed from the base 26 opposite the first surface 30, said second surface 40 converging with the first surface 30 at the anterior edge 28. Generally triangular side surfaces 50 and 60, having curved adjacent and hypotenuse edges, are thus evincible laterally delimiting the head member 20 on either side between the first and second surfaces 30, 40 (see for example FIGS. 1 and 2).

Figure 2:
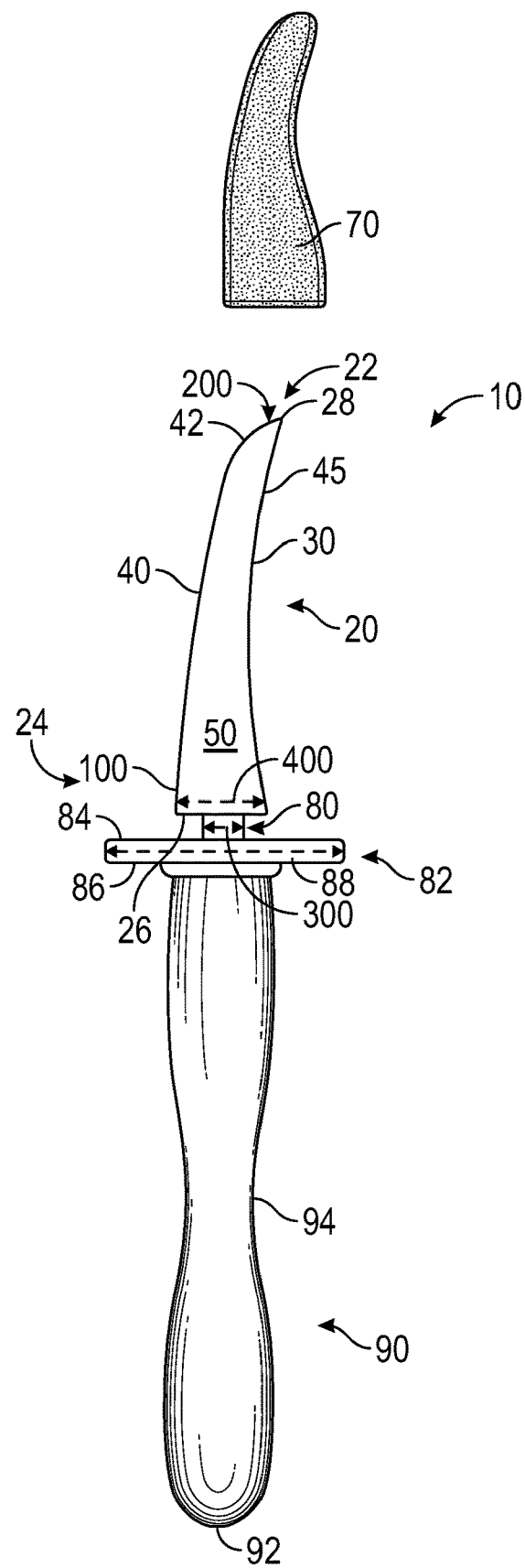
FIG. 2 is a side elevation view of an example embodiment.

In the example embodiment herein depicted, for example in FIGS. 1 and 2, the first surface 30 is convex and includes a parabolic coronal cross-section with a focus 33 disposed medially upon the anterior edge 28. In this embodiment, the slope of the first surface 30 is contemplated to steepen towards the base 26 whereby the derivative of the slope of the first surface 30 is not constant. The slope of the first surface 30 reverses direction at a central portion 45 more proximal the anterior edge 28.

The second surface 40, disposed opposite the first surface 30, also includes a parabolic coronal cross-section vertexed by focus 33 medially disposed at the anterior edge 28. The derivative of the slope of the second surface 40 is likewise not constant, although the slope of the second surface 40 is less steep than that of the first surface 30, at least until a convergent portion 42 increases in steepness towards the anterior edge 28 (see for example FIG. 2). The slope of the second surface is in one direction only, and is generally parallel the slope of the central portion 45 of the first surface 30.

The first surface 30 thus serves as a recurved scoop when a user extends the anterior edge 28 into the vestibule of said user's nose, said anterior edge 28 disposed terminally recurved from the base 26, enabling tactile engagement of the anterior edge 28 wielded as a leading point of contact against the respiratory epithelium interior to the nasal cavity 506.

Figure 5:
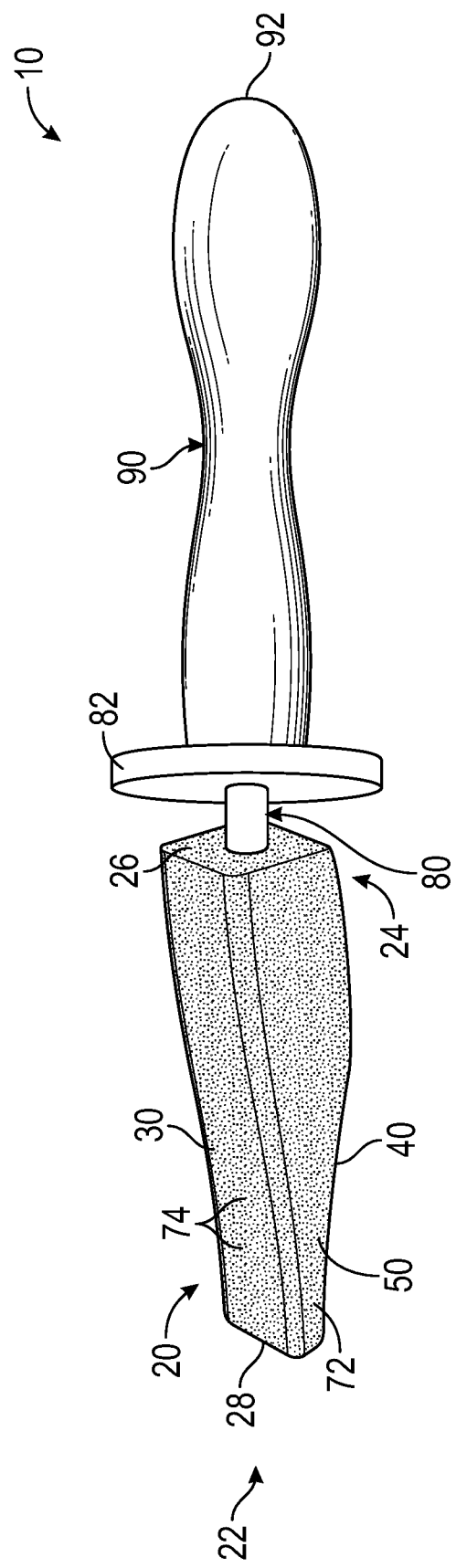
FIG. 5 is an isometric view of a head member devised coextensive with an absorbent layer.

In the embodiment illustrated in FIG. 5, the first surface 30 and second surface 40 maintain a constant slope and the head member 20 is therefore devised as a triangular prism.

Figure 3:
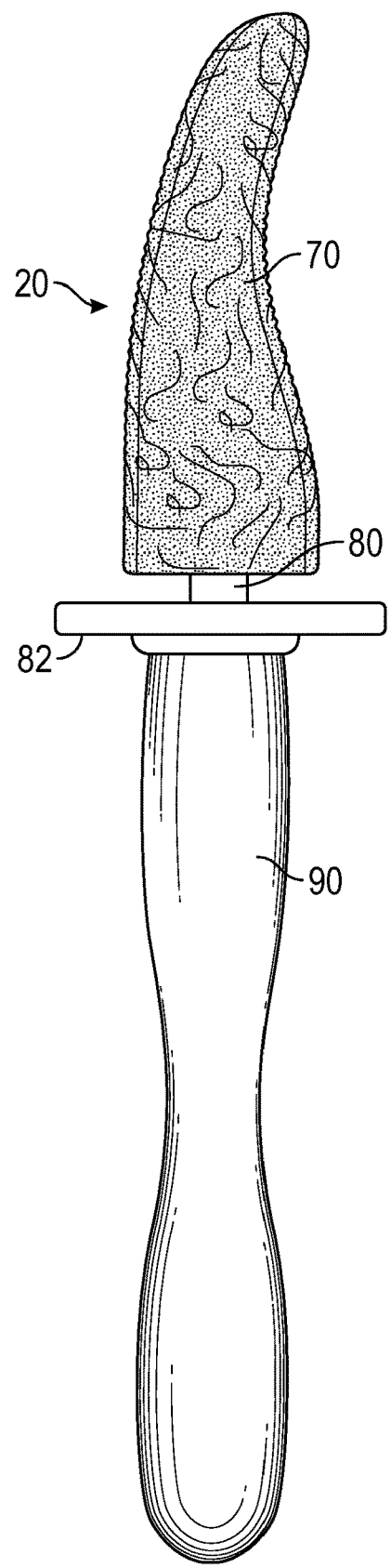
FIG. 3 is a side elevation view of an example embodiment having an absorbent layer disposed overtop a spatulate head member.
Figure 4:
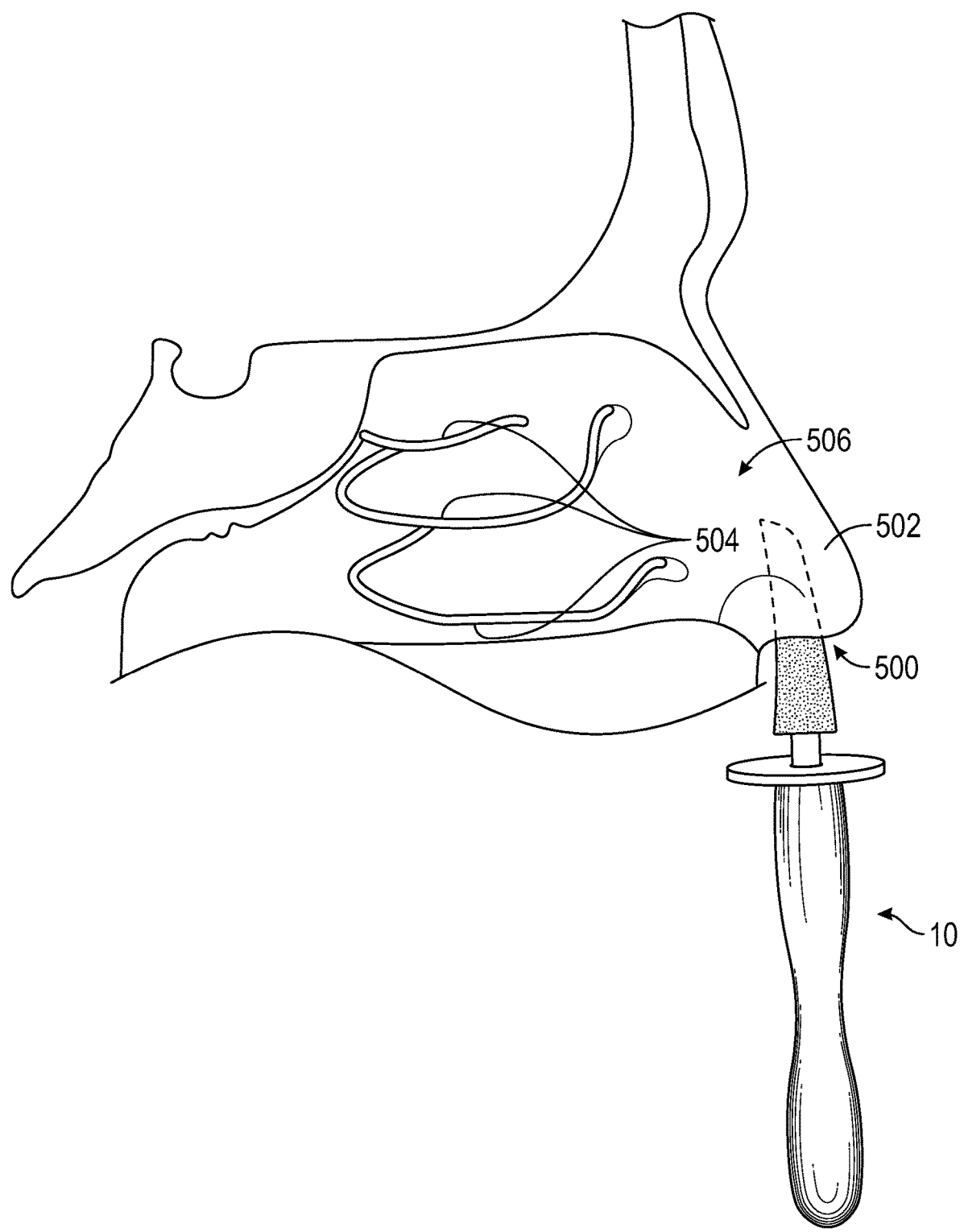
FIG. 4 is an in-use view.

In the example embodiment illustrated in FIGS. 1, 2, and 3, the absorbent layer 70 is disposed tautly covering the head member 20, at least upon the first and convex second 30, 40 and overtop the anterior edge 28. In the example embodiment depicted in FIGS. 1, 2, and 3, the absorbent layer 70 is flocculent and derived of cotton. However, it should be appreciated by one having ordinary skill in the art that any substance having a wicking potential and/or an osmotic potential suited to the absorbance of mucus when positioned in proximal contact interior the nasal cavity is contemplated as part of this disclosure. In some embodiments, the absorbent layer 70 may be removable from, or additional to, the head member 20. In the embodiment depicted in FIG. 5, the absorbent layer 70, derived of a sponge material 72, is coextensive with the head member 20. In the embodiment shown in FIG. 5, then, the sponge material 72 has a porosity wherein mucus is collectable interior to the sponge material 72 absorbed within a plurality of pores 74.

A neck portion 80 is disposed endwise perpendicularly conjunct the base 26. In the example embodiment depicted herein, the neck portion 80 is cylindrical and has a diameter 300 substantially lesser than a length 400 of the base 26 (see for example FIG. 2). The neck portion 80 may enable some limited play of the head member 20 thereupon.

A shield member 82 is disposed perpendicularly upon the neck member 80 distally relative to the head member 20. The shield member 82 includes a forward surface 84, disposed facing the head member 20, and a rearward surface 86, disposed facing away from the head member 20. An outer rim 88 is disposed radially projected delimiting the shield member 82 at a position exceeding any delimit of the base 26. The shield member 82 thus extends laterally beyond the confines of the head member 20 and prevents over-insertion of the head member 20 into the nasal cavity. A user is thus protected from inadvertent over-extension of the apparatus 10 into the nasal cavity whereby potential damage to the nasal conchae 504 or undesirable lodgment of the head member 20 within the nasal cavity 506 is preventable (see for example FIG. 4). Additionally, the planar extent of the shield member 82 shields a users hand while manipulating the posteriorly located handle member 90, described subsequently, from inadvertent contact with mucus. Cross-contamination is thereby also preventable.

The handle member 90 is longitudinally disposed endwise from the shield member 82 rearward surface 86. The handle member 90 is ergonomically configured for tactile engagement in the hand of a user. The handle member 90 therefore may be rubberlike for frictional engagement and increased dexterity in the hands of a user. In the example embodiment herein disclosed, the handle member 90 includes a rounded hyperboloidal longitudinal cross-section and a rounded proximal end 92 (see for example FIG. 2). A narrows 94 is disposed medially conjoining the handle member 90 at a minimum thickness thereof.

A user is therefore enabled tactility in wielding the rhinotillexis apparatus 10 when inserting the spatulate head member 20 into a naris 500 for collection of mucus from an associated vestibule 502 of the user. Mucus is therefore distally removable from the user's nasal cavity 506 without the user having to directly contact the respiratory epithelium, mucus membranes, or any portion of the nasal cavity 506 whereat contamination with mucus borne pathogens may be facilitated. Disposal of the apparatus 10 after a single-use further prevents contamination and associated cross-contamination.

What is claimed is:

1. A rhinotillexis apparatus comprising:
    a spatulate head member having a maximum thickness at a posterior end and a minimum thickness at an anterior end;
    a polygonal base disposed at the posterior end;
    an anterior edge disposed at the anterior end;
    a first surface disposed sloped from the base to the anterior edge;
    a second surface disposed opposite the first surface, said second surface disposed from the base convergent with the first surface at the anterior edge;
    a neck portion disposed posteriorly projected perpendicularly from the base;
    a shield member disposed transversely upon the neck portion, said shield member having an outer rim projected radially beyond any delimit of the base; and
    a handle member longitudinally projected posteriorly from the shield member;
    wherein the spatulate head member is enterable into a naris of a user for collection of mucus from a vestibule of the user, whereby mucus is distally removable from a nasal cavity of the user without direct contact by the user required.

2. The rhinotillexis apparatus of claim 1 wherein the spatulate head member further comprises an absorbent layer, said absorbent layer having an osmotic potential for sorption of mucus.

3. The rhinotillexis apparatus of claim 2 wherein the neck portion is cylindrical, said neck portion having a diameter lesser than a length of the base.

4. The rhinotillexis apparatus of claim 3 wherein the shield member is discoid and the outer rim is circular, said outer rim disposed upon a diameter larger than the length of the base.

5. The rhinotillexis apparatus of claim 4 wherien the handle member further comprises:
    a hyperboloidal longitudinal cross-section; and
    a rounded proximal end;
    wherein the handle member is ergonomically configured for tactility in use.

6. The rhinotillexis apparatus of claim 4 wherein the slope of the first surface steepens towards the base and changes direction at a central portion whereby the anterior edge is recurved relative the first surface.

7. The rhinotillexis apparatus of claim 4 wherein the absorbent layer is coextensive with the head member and comprises a sponge material having a plurality of pores.

8. The rhinotillexis apparatus of claim 4 wherein the absorbent layer is flocculent and removable from the head member.

9. The rhinotillexis apparatus of claim 8 wherein the absorbent layer is made of cotton.

10. A rhinotillexis apparatus comprising:
    a spatulate head member having a maximum thickness at a posterior end and a minimum thickness at an anterior end;
    a polygonal base disposed upon the spatulate head member at the posterior end;
    an anterior edge disposed at the anterior end;
    a first surface disposed sloped from the posterior end to the anterior end, said first surface having a parabolic coronal cross-section with a focus disposed medially upon the anterior edge;
    a second surface disposed opposite the first surface, said second surface converging with the first surface at the anterior edge;
    a cylindrical neck portion disposed perpendicularly conjunct the base;
    an absorbent layer disposed covering the head member;
    a discoid shield member disposed perpendicularly upon the neck member, said discoid shield member including:
        a forward surface disposed facing the head member;
        a rearward surface disposed facing away from the head member;
        an outer rim disposed radially projected beyond a delimit of the base;
    a handle member longitudinally disposed endwise from the shield member rearward surface, said handle member having:
        a hyperboloidal longitudinal cross-section;
        a medially disposed narrows; and
        a rounded proximal end;
    wherein the spatulate head member is enterable into a naris of a user for collection of mucus from a vestibule of the user, whereby mucus is distally removable from a nasal cavity of said user without direct contact by the user required.

11. The rhinotillexis apparatus of claim 10 wherein the absorbent layer is coextensive with the head member and comprises a sponge material having a plurality of pores.

12. The rhinotillexis apparatus of claim 10 wherein the slope of the first surface steepens towards the base and changes direction at a central portion whereby the anterior edge is recurved relative the first surface.

13. The rhinotillexis apparatus of claim 10 wherein the absorbent layer is flocculent and removable from the head member.

14. The rhinotillexis apparatus of claim 13 wherein the slope of the first surface steepens towards the base and changes direction at a central portion whereby the anterior edge is recurved relative the first surface.

15. The rhinotillexis apparatus of claim 13 wherein the absorbent layer is made of cotton.

16. The rhinotillexis apparatus of claim 14 wherein the absorbent layer is made of cotton.

* * * * *